(12) United States Patent
Wotton, III

(10) Patent No.: US 6,395,010 B1
(45) Date of Patent: May 28, 2002

(54) CRIMPING DEVICE FOR CRANIAL CRUCIATE LIGAMENT STABILIZATION

(75) Inventor: Harry Wotton, III, E. Brookfield, MA (US)

(73) Assignee: Securos, Inc., Charlton, MA (US)

( * ) Notice: Subject to any disclaimer, the term of this patent is extended or adjusted under 35 U.S.C. 154(b) by 0 days.

(21) Appl. No.: 09/537,651

(22) Filed: Mar. 29, 2000

Related U.S. Application Data

(60) Provisional application No. 60/172,918, filed on Dec. 21, 1999.

(51) Int. Cl.$^7$ .............................................. A61B 17/04
(52) U.S. Cl. ........................ 606/148; 606/103; 606/232
(58) Field of Search ................................ 606/232, 139, 606/141, 151; 81/424.5, 426.5; 72/409.19, 416; 128/897–899

(56) References Cited

U.S. PATENT DOCUMENTS

| | | | | |
|---|---|---|---|---|
| 4,128,100 A | * | 12/1978 | Wendorff | 606/141 |
| 5,042,285 A | * | 8/1991 | Levy | 72/410 |
| 5,545,168 A | * | 8/1996 | Burke | 606/74 |
| 5,669,917 A | * | 9/1997 | Sauer et al. | 606/139 |
| 5,741,260 A | * | 4/1998 | Songer et al. | 606/74 |
| 6,017,347 A | * | 1/2000 | Huebner et al. | 606/74 |

* cited by examiner

Primary Examiner—Kennedy Schaetzle
Assistant Examiner—Kristen Droesch
(74) Attorney, Agent, or Firm—Hamilton, Brook, Smith & Reynolds, P.C.

(57) ABSTRACT

A cranial cruciate ligament stabilization system comprises of a surgical tensioning device that applies accurate and precise tension to the suture, a surgical implant crimp clamp when crimped secures the suture and a crimping device that accurately and precisely crimps the surgical crimp clamp. The tensioning device is placed over the suture once the crimp clamps are positioned. The surgeon than squeezes the handle that will in turn open the distal tips., therefore, applying tension to the suture. The tensioning device, having a ratcheting mechanism, allows for the surgeon to test for the appropriate tension through out the tensioning process. Once the desired tension is achieved the surgeon will crimp the primary or center crimp clamp, which is already in place, using the crimping device. The crimp clamp has physical and mechanical properties that ensures that it can be crimped simply and hold it's deformed state once it is crimped. The crimping device has specific geometry within each of its jaws. The geometry ensures that the crimping device will crimp the crimp clamp the exact amount so not to over crimp the crimp clamp and break the suture nor under crimp the crimp clamp allowing the suture to slip within the crimp clamp.

20 Claims, 13 Drawing Sheets

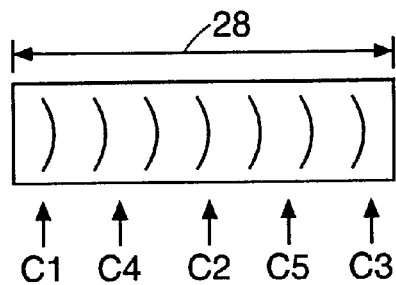
FIG. 2
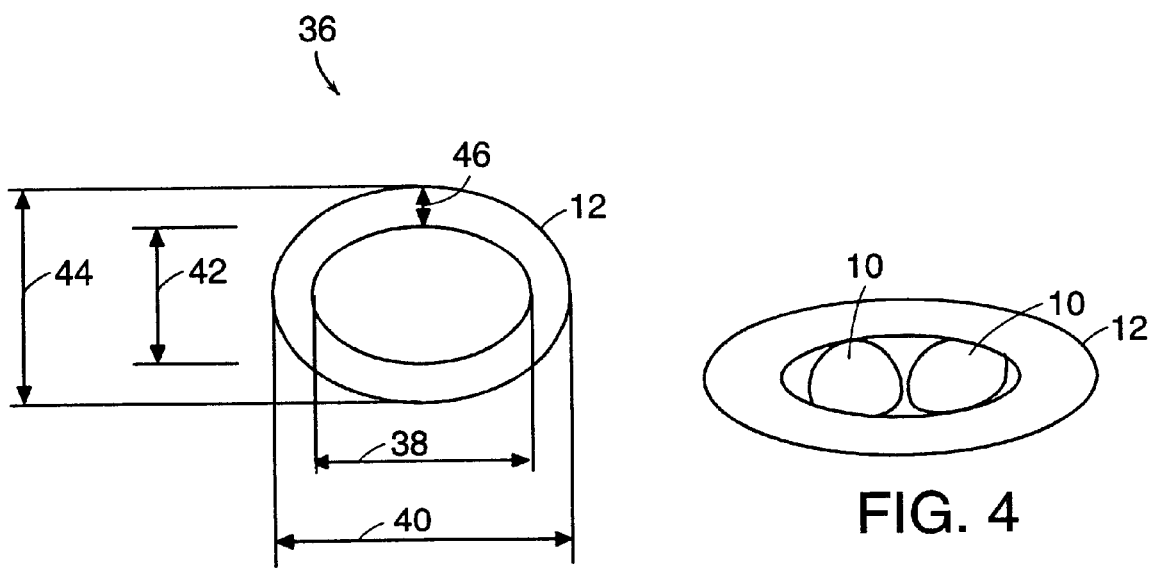
FIG. 3
FIG. 4
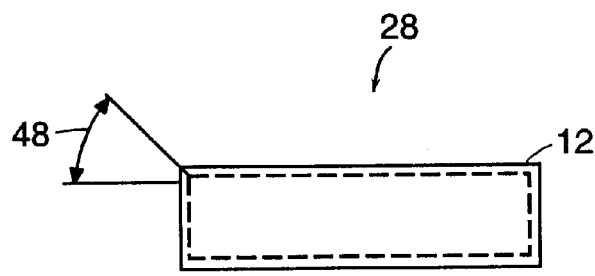
FIG. 5

CRIMPING DEVICE FOR CRANIAL CRUCIATE LIGAMENT STABILIZATION

RELATED APPLICATION

This application claims priority to U.S. Provisional Application No. 60/172,918 filed Dec. 21, 1999, the entire teachings of which are incorporated herein by reference.

This application is related to copending application Ser. No. 09/537,521 filed Mar. 29, 2000, entitled TENSIONING DEVICE FOR CRANIAL CRUCIATE LIGAMENT STABILIZATION, by Harry Wotton, III, the entire teachings of which are incorporated herein by reference.

BACKGROUND OF THE INVENTION

Cranial Cruciate (anterior cruciate) ligament stabilization systems are used on knees that have been traumatized resulting from excess interior rotation or excess cranial movement of the femur in respect to the tibia. An incision is made through lateral aspect of the stifle. The dermis layer is retracted in order to have adequate room to place the lateral suture. The lateral suture is placed, extra-articular, around the lateral fabella and through a hole drilled in the tibial tuberosity or distal patella tendon. The two ends of the suture are than placed through a surgical crimp clamp (primary crimp clamp). Two additional crimp clamps (secondary crimp clamps) are added to the ends that were placed through the primary crimp clamp. Tension is applied, using the secondary clamps as an anchoring point, to the loop. Once the appropriate tension is reached the crimping tool is used to crimp the primary crimp clamp. The secondary crimp clamp are removed and the incision is closed.

The DeAngelis (lateral suture) technique is commonly used in veterinary orthopedic surgery. This technique also places the suture around the lateral fabella and through a hole in the tibial tuberosity. Once the suture is in position the surgeon has to physically pull on the ends of the suture to acquire the desired tension and an assistant must clamp down on the two strands to maintain that tension. After clamping on the suture the surgeon will tie a knot, which will secure the nylon.

The DeAngelis technique does not allow for the accurate adjustment of tension to the stifle joint, it does not maintain the desired loop tension in the suture, and it does not allow larger suture material to be used. This is because the DeAngelis technique requires the surgeon to create the tension, in the suture loop, using physical strength. Therefore it is hard to acquire the adequate/precise tension. Published data shows that 10–15% of the loop tension is lost after the first throw and an additional 10–15% is lost when the dog starts to use the limb (the knot tightens). Also, due to the fact that a knot must be tied there is a limit on the size and strength of the material that can be used due to the suture resistance to bending, the memory of the material and the size of the resulting knot.

The DeAngelis/Lateral suture technique is particularly susceptible to loosening under repeated cyclic loading. The lateral suture technique relies entirely on the knot to preclude loop elongation. A slight amount of loosening due to cyclic loading reduces loop tension in the suture allowing internal rotation and cranial movement of the femur, which would result in lameness of the patient.

SUMMARY OF THE INVENTION

The present invention is directed to a tensioning instrument that applies the appropriate tension to the loop and secures the suture so not to allow any loop elongation. The tensioning device includes a first tensioning arm having a proximal end and a distal end, a second tensioning arm having a proximal end and a distal end, a first slot located in the distal end of the first tensioning arm, the first slot allowing for holding of a suture and a second slot located in the distal end of the second tensioning arm, the second slot allowing for holding of a suture. The first tensioning arm is hingedly connected to the second tension arm. The distal end of the first and second arms can form a bend relative to the proximal end of the first and second arms, where the bend allows a user to insert the tensioning device into an incision site.

Preferably, the tensioning device will apply the appropriate tension, maintaining that tension while the surgeon checks the joint for movement. The tensioning device has an angle and slots at the distal tips so that the tips may slide over the suture and apply the tension against the secondary crimp clamps. The angle stops crimp clamp from sliding off the instrument. The crimp clamps are used in place of a knot to secure the suture, significantly reducing loop elongation. The crimp clamp has an oval cross section to allow the desired suture to be place through its center and a specific material properties and wall thickness so that once it is crimped it will stay crimped. Further, a crimping tool is designed so that the exact amount of crimp is applied to the crimp clamp. The dimensions of the crimping area on the crimp tool are such that the crimp tool does not over crimp the suture, which would sever the material, nor does it under crimp the suture, allowing it to slip in the crimp tube. If one tried to crimp a tube using an instrument that was not specifically designed for crimping it would either over crimp the nylon that would cause the nylon to break or it would under crimp the nylon allowing it to slip.

Specifically, the tensioning device has an angle and slots at its distal tips. The slots allow the suture to be placed into the tips of the instrument allowing the secondary crimp clamps to rest against the outer edge of the tip. The angle ensures that the secondary crimp clamp will not slip off the tip during tightening. Preferably, there are ratchets in the handle of the instrument that locks the instrument at a variety of locations, therefore tension can be applied and than checked by the surgeon to ensure adequate tension in the joint. The angled tips of the tensioning device also allow the tool to function as a device to open up the joint to assess the damage and clean out any scare tissue.

The surgical implant crimp clamps have a specific cross section, specific material properties pertaining to the strength of the clamp, and a specific wall thickness that ensures the clamp can be crimped easily enough and hold its deformed state. The cross section is oval shaped allowing the appropriate size suture to be used for the size of animal. The material properties combined with a specific wall thickness ensure that once the clamp is crimped it will maintain the appropriate tension on the suture so that the suture will not slip on break.

The present invention also relates to a crimp tool for use with the crimp having a first arm and a second arm, the first arm having a proximal end and a distal end, the proximal end comprising a handle and the distal end comprising a first jaw and the second arm having a proximal end and a distal end, the proximal end comprising a handle and the distal end comprising a second jaw. The crimp tool also includes a first crimping member integral with the first jaw of the first arm and a second crimping member integral with the second jaw of the second arm. The first arm of the crimp tool is hingedly connected to the first arm;

The crimping tool has oval like areas at each jaw. The dimensions of these oval or radius areas are specific to the crimp clamp being used. The dimensions are such that when the jaws are fully closed the crimp clamp is deformed a specific amount. This ensures that the crimp clamp will not be over crimped, therefore severing the suture and also ensures that the crimp clamp will not be under crimped allowing the suture to slip inside the clamp. The crimping tool is double action, which means there are two pivot points on the tool. This allows the surgeon to crimp the clamp with a fraction of the force that would be necessary if the tool was not double action. This feature of the tool removes the need for appropriate hand strength to fully crimp the clamp.

The present invention also relates to a surgical instrumentation kit having a surgical crimp tube for securing a suture, a tensioning device to adjust the tension of the suture and a crimping tool to crimp the surgical crimp tube over the suture.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 2. is a perspective, enlarged view of the long aspect of the inventive crimp clamp;

FIG. 3. is a cross-sectional view of the crimp clamp, showing the oval shape and wall thickness;

FIG. 4. is a cross-sectional view of the crimp clamp, showing the result after the clamp is crimped on the suture;

FIG. 5. is a front view of the crimp clamp showing the dimensions of the chamfered edge of the internal diameter, which stops the edge from damaging the nylon;

DETAILED DESCRIPTION OF THE PREFERRED EMBODIMENTS

Figure 1:
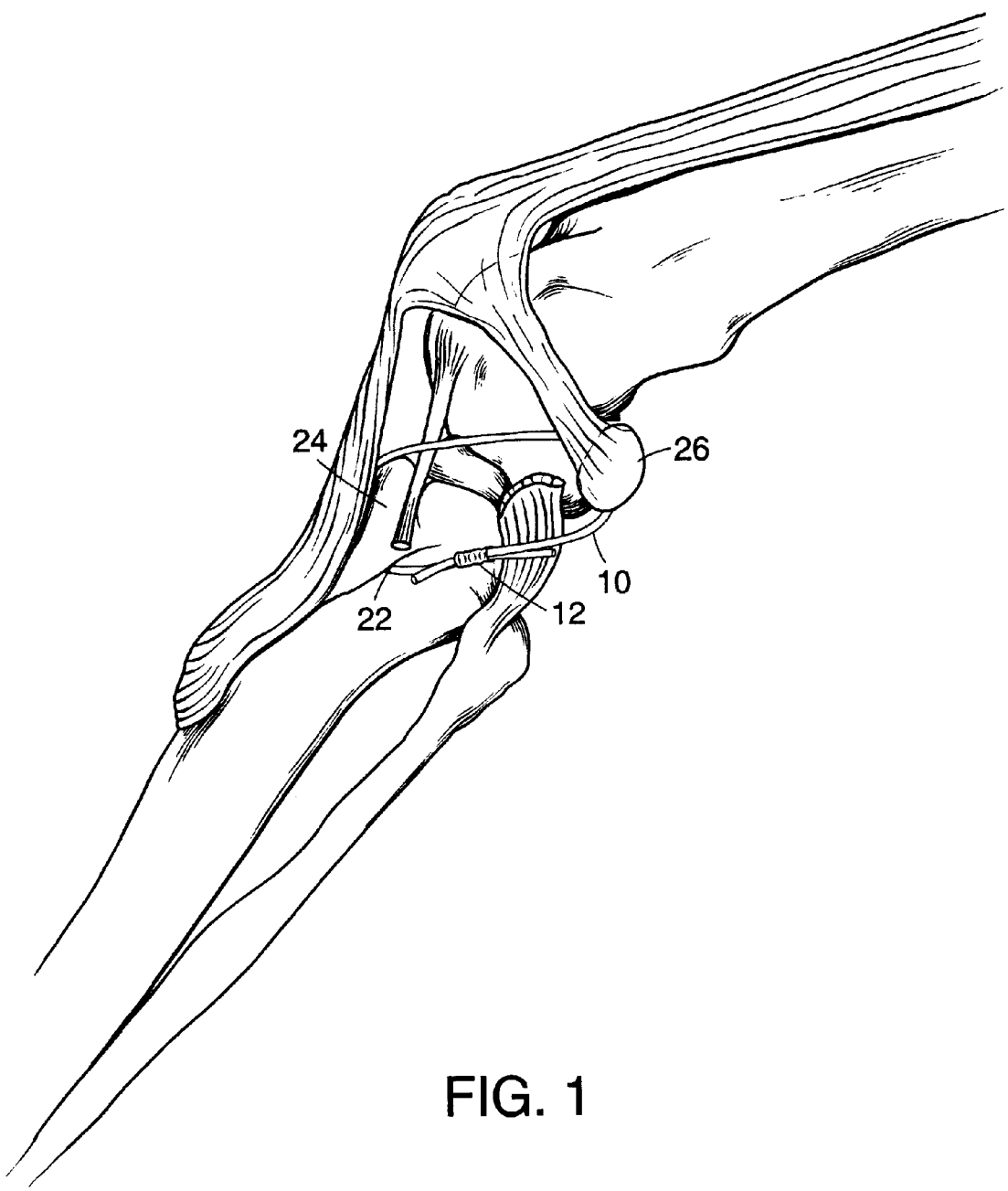
FIG. 1. is a perspective view of a lateral suture secured with the surgical crimp clamp. The illustration shows the location of the suture and crimp clamp relative to the anchoring points in the tibial tuberosity and around the lateral fabella.

FIG. 1 is a perspective view of a lateral suture 10 used to stabilize the canine stifle incorporating a surgical crimp tube or clamp 12 that is used in place of a knot and the 80 lb. monofilament nylon. As is common in this technique, the monofilament nylon 10 is placed through a hole 22, which was drilled in the tibial tuberosity 24, and around the lateral fabella 26 using specially designed suture needles. The suture 10 is a hard type monofilament nylon with a tensile strength of 80 lbs. However, other sizes and brands of nylon are also commonly used. The surgical crimp clamp 12 is produced from implant grade, surgical stainless steel. The inside diameter edges of the crimp clamps have a slight chamfer, which is necessary, so that when the tube is crimped it will not damage the nylon.

The most extreme stresses occur once the animal starts to use the limb. When using a knot to secure the suture 10, this leads to premature loop elongation due to the knot becoming tighter. When this occurs the animal will most likely show signs of lameness. Therefore, it is beneficial to use the crimp clamp 12, which does not allow any loop elongation. The tension that is observed in the operating room is what remains.

FIG. 2 is a enlarged view of the long aspect of the inventive crimp clamp 12. The length of the tube 12 along its long axis 28 is a critical dimension that allows the minimum amount of crimp to be applied so that the nylon will not slip. The crimps are placed in the direction of the "oval" geometry, i.e., transversely to the clamp's axis. It is recommended that the surgeon place a minimum of 3 crimps C1–C3 and a maximum of 5 along the long axis of the crimp tube. The crimps are placed one in the middle and one on either end. When crimping five times the additional two crimps C4–C5 are placed between the two end crimps and the middle crimp. The dimension of the long axis 28 of the crimp clamp 12 can be 0.278 inches. This dimension was determined by testing the tubes to determine the ideal length that would allow the required amount of crimps.

FIG. 3 is a cross-sectional view of the crimp clamp 12. The oval shape 36 is necessary so that the large diameter monofilament nylon suture 10 can be placed through the clamp 12. The horizontal dimension 38 of the crimp clamp 12 is such that it exceeds twice the diameter of the largest monofilament nylon suture 10 used in the described procedure. This is necessary because both ends of the suture 10 must pass through the crimp clamp 12. The vertical dimension 42 of the crimp clamps 12 is slightly larger than the largest diameter monofilament nylon suture 10 used in the described procedure. The vertical inner diameter 42 can be 0.073 inches while the vertical outer diameter 44 can be 0.113 inches. The horizontal inner diameter 38 can be 0.100 inches while the horizontal outer diameter 40 can be 0.140 inches.

The wall thickness 46 is also shown in FIG. 3. The wall thickness 46 is the value obtained when the inside diameter is subtracted from the outside diameter, then divided by two.

This wall thickness 46 value for the inventive crimp clamp 12 has to be very precise. The wall thickness 46 cannot be too large or it will be very difficult to crimp the clamp 12 with a the crimping tool. It also cannot be too small or the crimp will not adequately hold down on the suture 10. The wall thickness 46 must also be consistent down the long axis 28 of the crimp clamp 12 so to ensure that the crimp will hold at all crimp locations. The wall thickness 46 can be 0.020 inches, for example.

FIG. 4 is a cross-sectional view of the crimp clamp 12 after the clamps have been crimped with the inventive instrumentation. The illustration shows the deformation of the nylon 10 due to crimping the crimp clamp 12. The amount of deformation has to be very precise. If the nylon 10 is deformed too much, a stress riser will occur at the deformed area that will cause the suture to break at low loads. If the deformation is too little, the suture 10 will slip at low loads. If either of these two actions happen it is most likely that the animal will show signs of lameness.

FIG. 5 is the front view of the crimp clamp 12 showing a chamfer 48 which is an angle that is put on the inner diameter edge of the crimp clamp 12. The chamfer 48 can have dimensions of 45° relative to the long axis 28 of the clamp 12, which is necessary so as not to damage the suture 10 during application.

Figure 6:
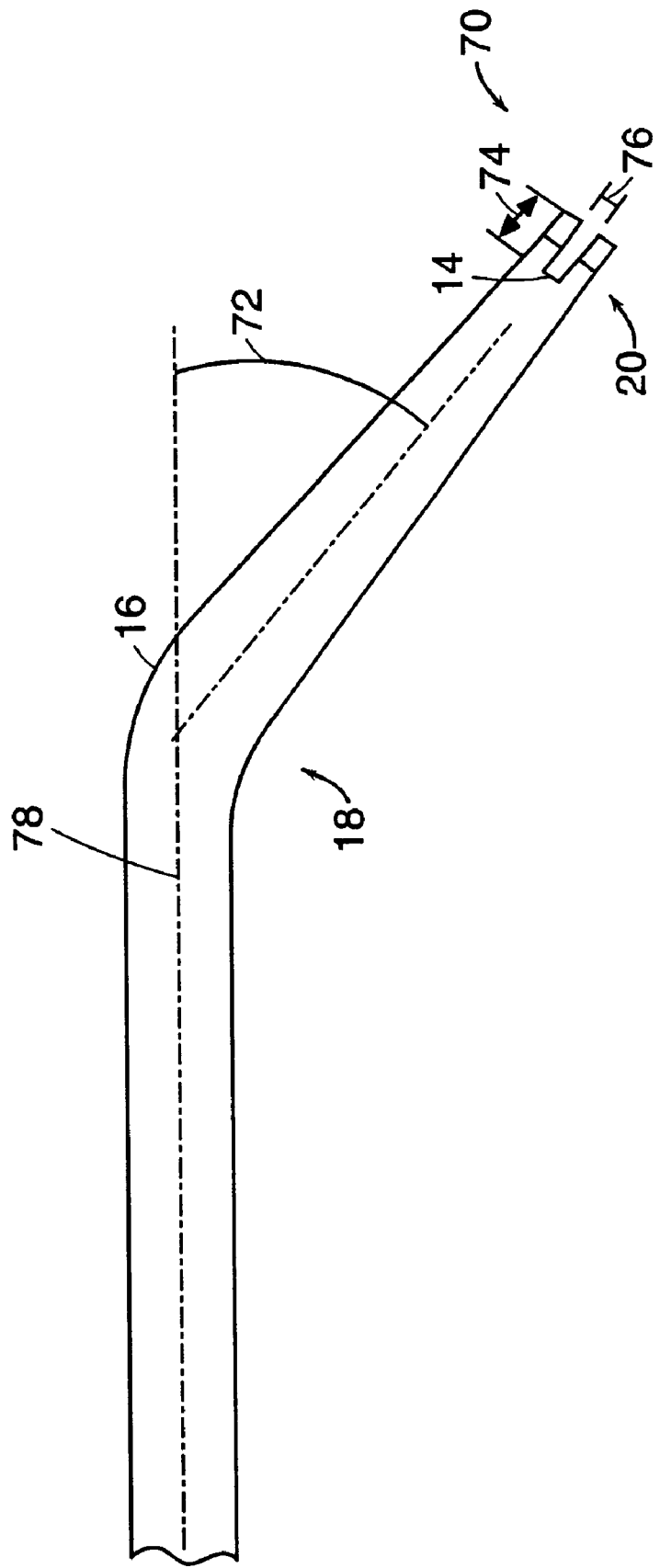
FIG. 6. is an enlarged partial side view of the tensioning device showing the slot, bend at the distal tips and the major bend located before the distal tips of the instrument.

FIG. 6 is an enlarged side view of a tensioning device 16 that illustrates slots 14 at the distal tip 70, an angle or bend 20 at the distal tip 70 and a bend 18 before the tips 70. The slots 14 are wider than the largest suture 10 that would be used in the procedure. Because the slots 14 are larger than the suture material 10 it allows the tensioning tool 16 to be easily applied over the nylon suture 10. The slots 14 have to be free of sharp edges so that the nylon suture 10 is not damaged during the tensioning process. The length of the slots 14 is such that when the tensioning device 16 is applied over the suture 10 there is enough room to allow the crimp clamp 12 to rest firmly against the sides of the tips 70.

The angle 18 at the distal tips 70, of a certain degree, is used to keep secondary crimp clamps from slipping off the tips 70 during the tensioning process. When the tensioning tool 16 is placed over the suture 10 between the primary crimp clamp 12 and the secondary crimp clamps, the secondary crimp clamps lie below the angle on the distal tips 70. The bend 20 located before the distal tips 70 is such that the tool can be easily inserted into an incision site and over the suture 10.

The relevant dimensions of the slot can include a slot width 76 of 0.063 inches and a slot length 74 of 0.125 inches. The angle 18 can begin 0.063 inches from the end of the distal tips 70. The major bend 18 can form an angle of 45° relative to the long axis 78 of the tensioning device 16.

Figure 7:
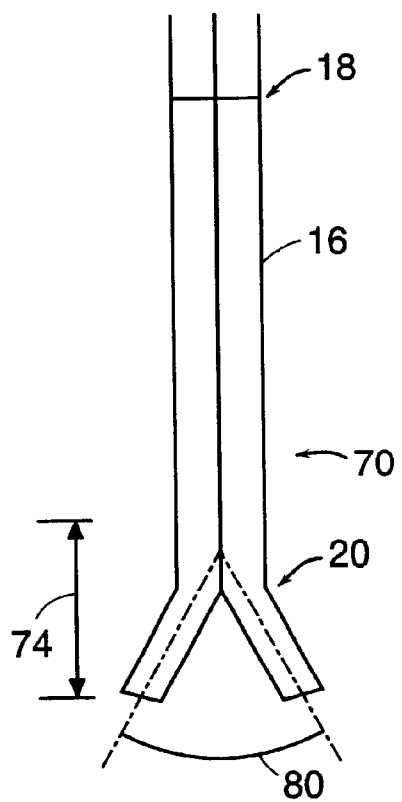
FIG. 7. is a enlarged partial top view of the tensioning device showing the slots and angle at the distal tips of the instrument.

FIG. 7 is an enlarged top view of the tensioning device 16 showing the length 74 of the slots and the angle 80 of the bend 20. The angle 80 of the bend 20 can be a 60° angle, for example.

Figure 8:
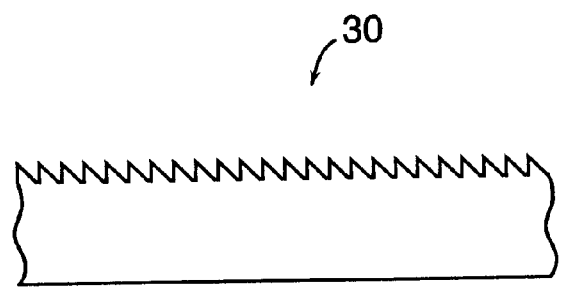
FIG. 8. is an enlarged top view of the ratcheting mechanism in the handles of the tensioning device.

FIG. 8 is an enlarged top view of a ratcheting mechanism 30 in the handles of the tensioning tool 16. The geometry of the ratchet 30 allows the device to apply a controlled amount of tension to the suture 10. Closing the handles and advancing them one ratchet at a time produces more tension at every location. By having a tensioning device 16 that locks or holds its position, the surgeon can palpate the joint and move the limb through its range of motion before securing the suture. The ratcheting mechanism 30 also allows the surgeon to perform the procedure without an assistant. The typical procedure required the surgeon to use physical strength to apply the tension and while the surgeon was pulling the suture tight an assistant needed to grab hold of the nylon to hold it in position. When the assistant grabs hold of the suture there is a likelihood that the suture will break. This is not an issue when using the tensioning device 16.

Figure 9:
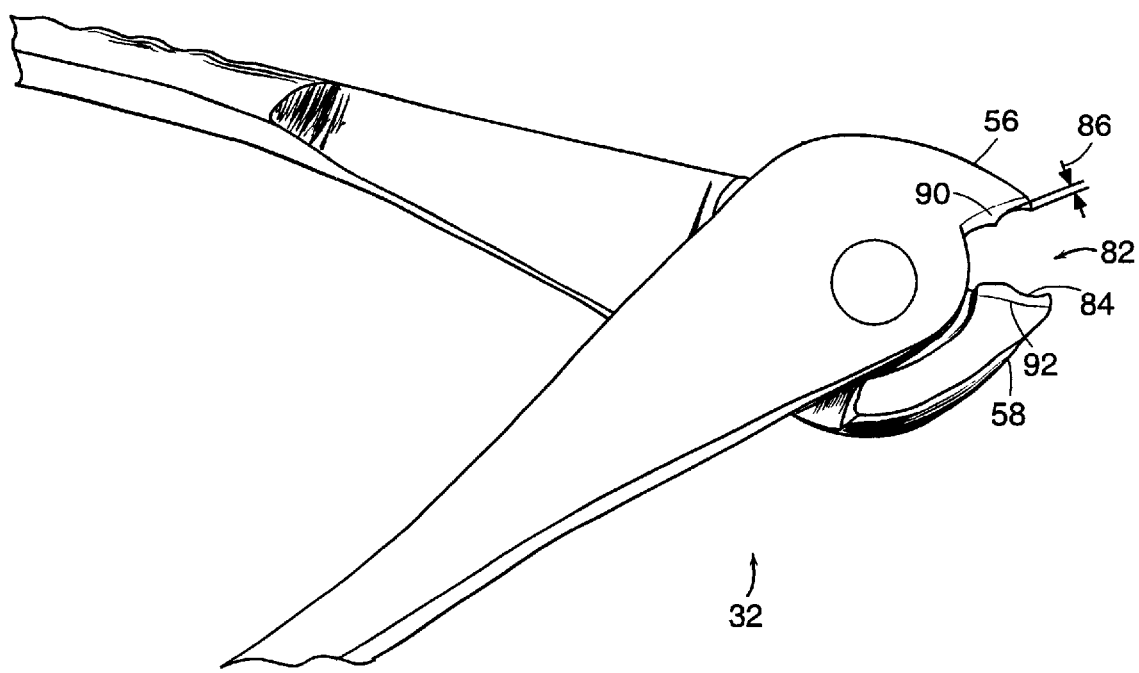
FIG. 9. is an enlarged side view of the crimping tool showing the geometry of the crimping area and tips.

FIG. 9 is an enlarged side view of a crimping tool 32 illustrating the geometry of the crimping area 82 located in the jaws 56, 58 of the instrument 32. The first 56 and second 58 jaws have a first crimping member 90 and a second crimping member 92 integral with the jaws 56, 58, respectively, which include identical, but mirror image, curved radii. The inner surface 84 of the curved radii are smooth and free from sharp edges. The width 86 of the inner surface 84 of the radii determines the width and amount of deformation the suture will under go. The crimping tool 32 can have an inner surface width 86 of 0.059 inches. The surface of the crimping area 82 must not be sharp or too narrow or the suture will be cut when it is crimped. Too wide of an area would make it difficult to crimp the tube. The geometry of the crimping area 82 does not cause a significant stress riser at the crimp site on the nylon 10.

The length between the highest points of the crimping area, when the jaws 56, 58 are closed, are the dimensions that allow the crimping tool 32 to crimp the clamp 12 and nylon 10 the right amount. If this dimension was increased or decreased the nylon 10 would either slip or break after crimping. The length of the crimping area is also specific. The length is such that when the crimping tube 12 is crimped the two strands 0f suture 10 a pushed inward toward each other allow friction to be created between the two strands, therefore enhancing the holding power of the crimp clamp 12.

Figure 10:
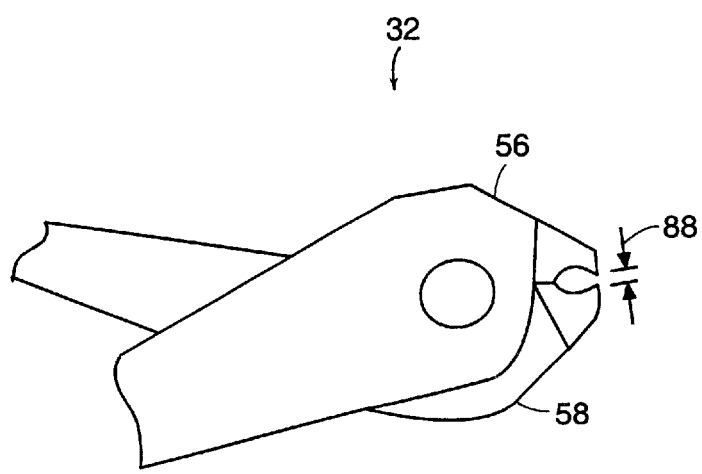
FIG. 10. illustration of the inventive instrumentation involved in the described procedure.

FIG. 10 is an enlarged frontal view of the tip of the jaws of the crimping tool 32 in a closed position. There is a gap 88 between the jaws 56, 58 at the most distal portion when the crimping tool 32 is fully closed. The gap can have a width of 0.025 inches. Having this gap 88 present removes the possibility that the surgeon may pinch some soft tissue with the tips and also removes the possibility that the surgeon may cut the nylon with the tips.

Figure 11:
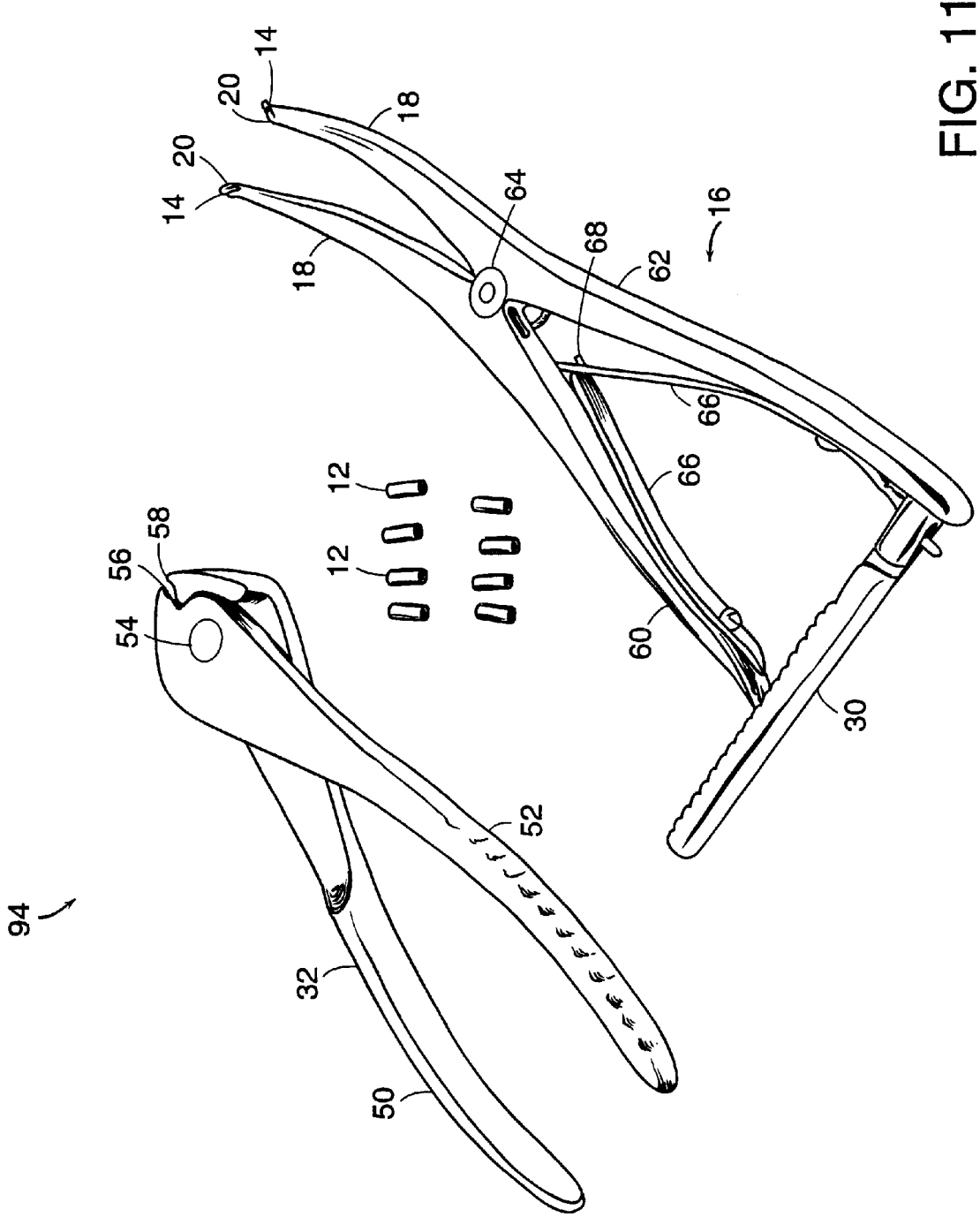
FIG. 11. is an enlarged view of the crimping tool showing the relevant dimensions of the tip of the crimping area.

FIG. 11 illustrates instrumentation involved in a procedure for tensioning a suture, in the form of a kit 94. The kit 94 can include a crimping device 32, crimp clamps 12 and a tensioning device 16.

Specifically, the crimping device 32 comprises a first lever arm 50 and a second lever arm 52, which are hinged at a hinge point 54 in the manner of plyers. On the distal side of the hinge point is a first jaw 56, which is part of the second lever arm 52 and a second jaw 58, which is part of the first lever arm 50. The crimping device 32 can also include a double action mechanism which removes any constraints on a user's hand strength.

Figure 12:
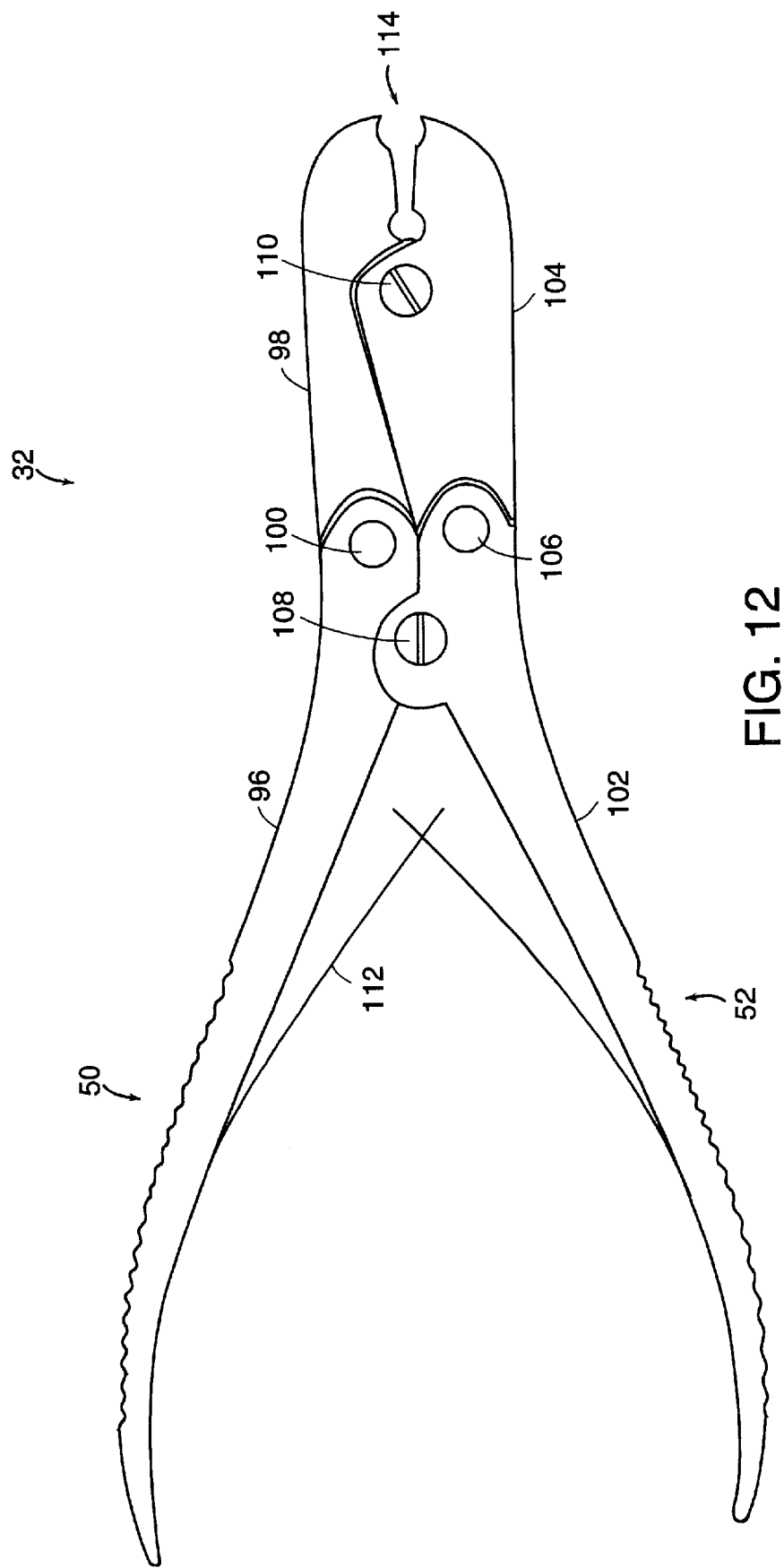
FIG. 12. shows a crimping device having a double action mechanism.

FIG. 12 illustrates a crimping device 32 having a double action mechanism. The crimping tool 32 has a first arm 50 and a second arm 52. A pair of spring arms 112 can be located between the first arm 50 and the second arm 52 to help bias the arms 50, 52 apart, to an open position. The first arm 50 has a proximal segment 96 and a distal segment 98 joined together by a pivot point or hinge 100. Similarly, the second arm 52 has a proximal segment 102 and a distal segment 104 joined together by a pivot point or hinge 106. For both the first arm 50 and the second arm, the proximal segments 96, 102 are longer than the distal segments 98, 104. The proximal segments 96, 102 form the handle of the crimping device while the distal segments 98, 104 form the jaws 114 of the device 32. Each jaw has a crimping area for crimping the crimp clamp, as described above. The crimping tool 32 having a double action mechanism also includes a first pivot 108 and a second pivot 110 between the first arm 50 and the second arm 52. The first pivot 108 connects the proximal segments 96, 102 of the device 32 and the second pivot 110 connects the distal segments 98, 104 of the device 32.

The double action mechanism works as follows. When the handle formed by proximal segments 96, 102 of the first arm 50 and second arm 52 is squeezed together, the proximal segments 96, 102 rotate about pivot 108 and move apart from one another at pivot points 100 and 106. This action, in turn, rotates the distal segments 98, 104 about pivot 110 thereby closing the jaws 114. The force seen at the jaws 114 is much greater than that seen at the jaws of a standard crimper, for the same amount of pressure applied to the handles.

The advantage of using a tool with a double action mechanism is that it reduces the force required by the surgeon to close the instrument by approximately half. The amount of hand strength required by the surgeon when crimping the crimp clamp can therefore be reduced.

Also included in the kit are multiple crimp clamps 12, in addition to the crimping tool 32. The crimp clamps can be made from a biologically compatible material, such as stainless steel.

The kit further comprises the tensioning device 16. The tensioning device 16 also comprises a first lever arm 60 and a second lever arm 62. These two lever arms 60,62 are connected at a hinge point 64. The hinging is such that when the proximal ends of the lever arms 60,62 are squeezed together by the user, the distal ends, at which the slots 14 are located, are spread apart from each other. Also, included at the proximal end of the lever arms 60,62 are two spring arms 66. These spring arms are rigidly connected to each of the lever arm 60,62. They engage each other at an engagement pivot point 68. They have the effect of urging the proximal ends of the lever arms away from each. As a result, when the proximal ends of the lever arms 60,62 are squeezed together by the user, the ratcheting system 30 locks the device in an open position. The ratcheting mechanism comprises the saw tooth ratchet arm 30, which is rigidly connected to the second lever arm 62 and engages the end tip of the first lever arm 60.

FIGS. 13–18 illustrate the steps involved in the procedure for tensioning a suture.

Figure 13:
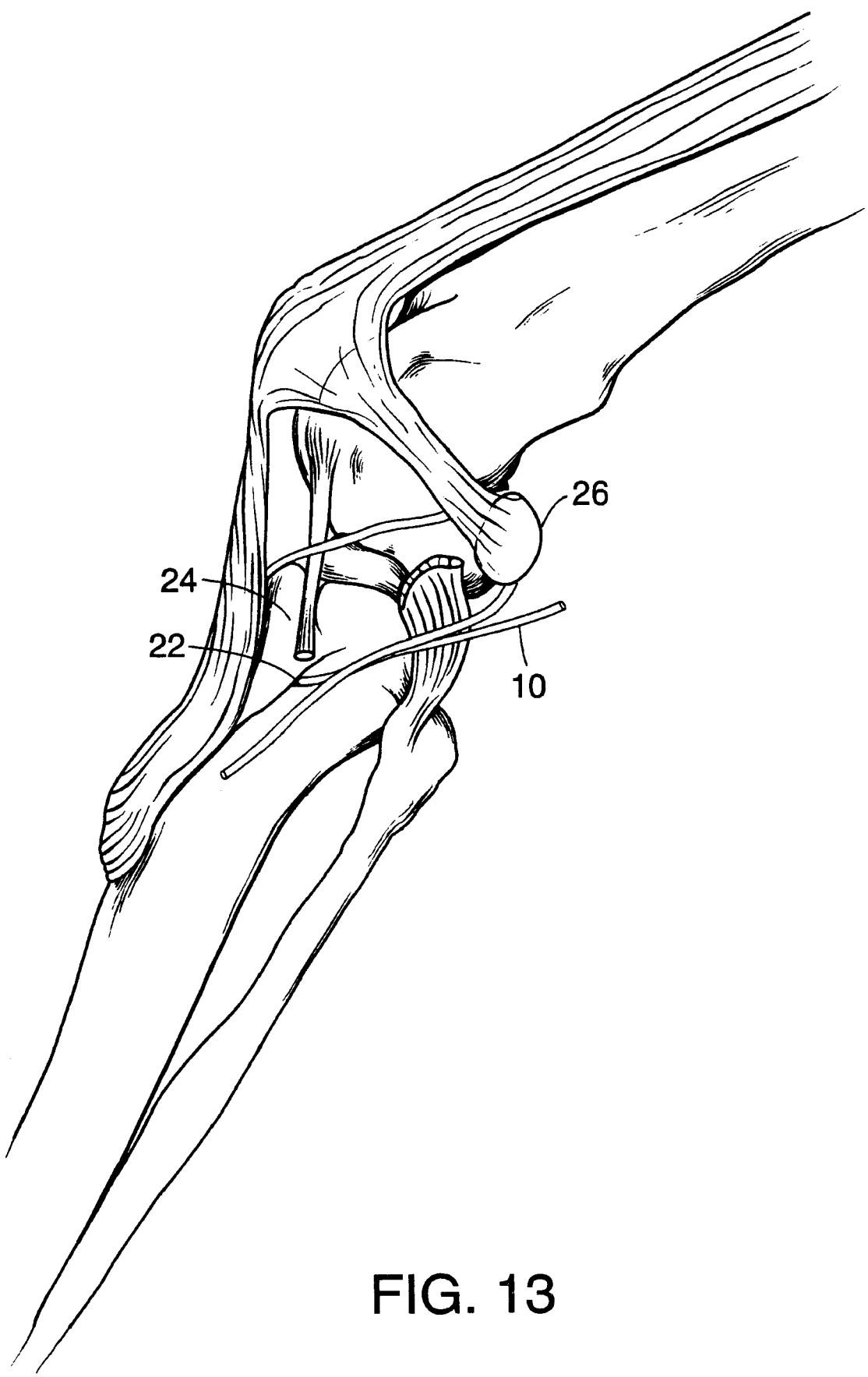
FIG. 13. illustration of step one of the surgical process.

FIG. 13 shows Step 1A of the procedure where the 80# monofilament nylon suture 10 is placed extra-articular using the DeAngelis technique. The user places the suture loop around the lateral fabella 26 and through the tibial tuberosity 24 or distal patella ligament. FIG. 13 shows the monofilament nylon suture 10 placed around the lateral fabella 26 and through a hole 22 drilled in the tibial tuberosity 24. For very large dogs the user may want to use a lateral and medial suture. Also this procedure is an extra-articular technique. For illustration only, the figure does not show any soft tissue.

Figure 14:
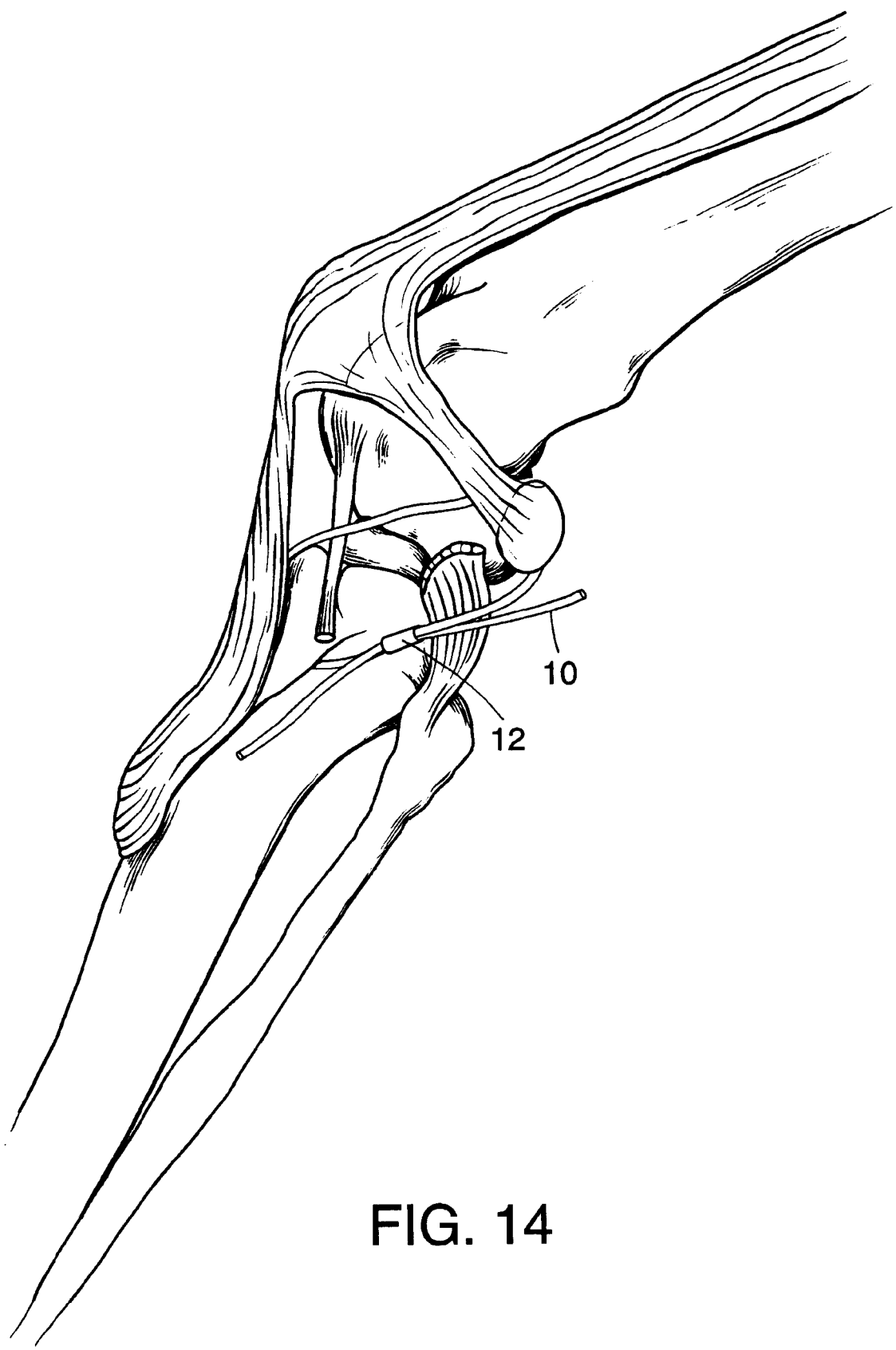
FIG. 14. illustration of step two of the surgical process.

FIG. 14 shows Step 2 of the procedure where the user slides one suture end at a time through one of the surgical crimp tubes 12. Once both ends have been placed through the surgical crimp tube 12, the user pulls the ends of the suture 10 so that the loop becomes taught. The user can then move the crimp tube 12 to the location illustrated in FIG. 14. Some surgeons like to place the crimp tube 12 in other locations, the location being subject to the specific surgeon's preference.

Figure 15:
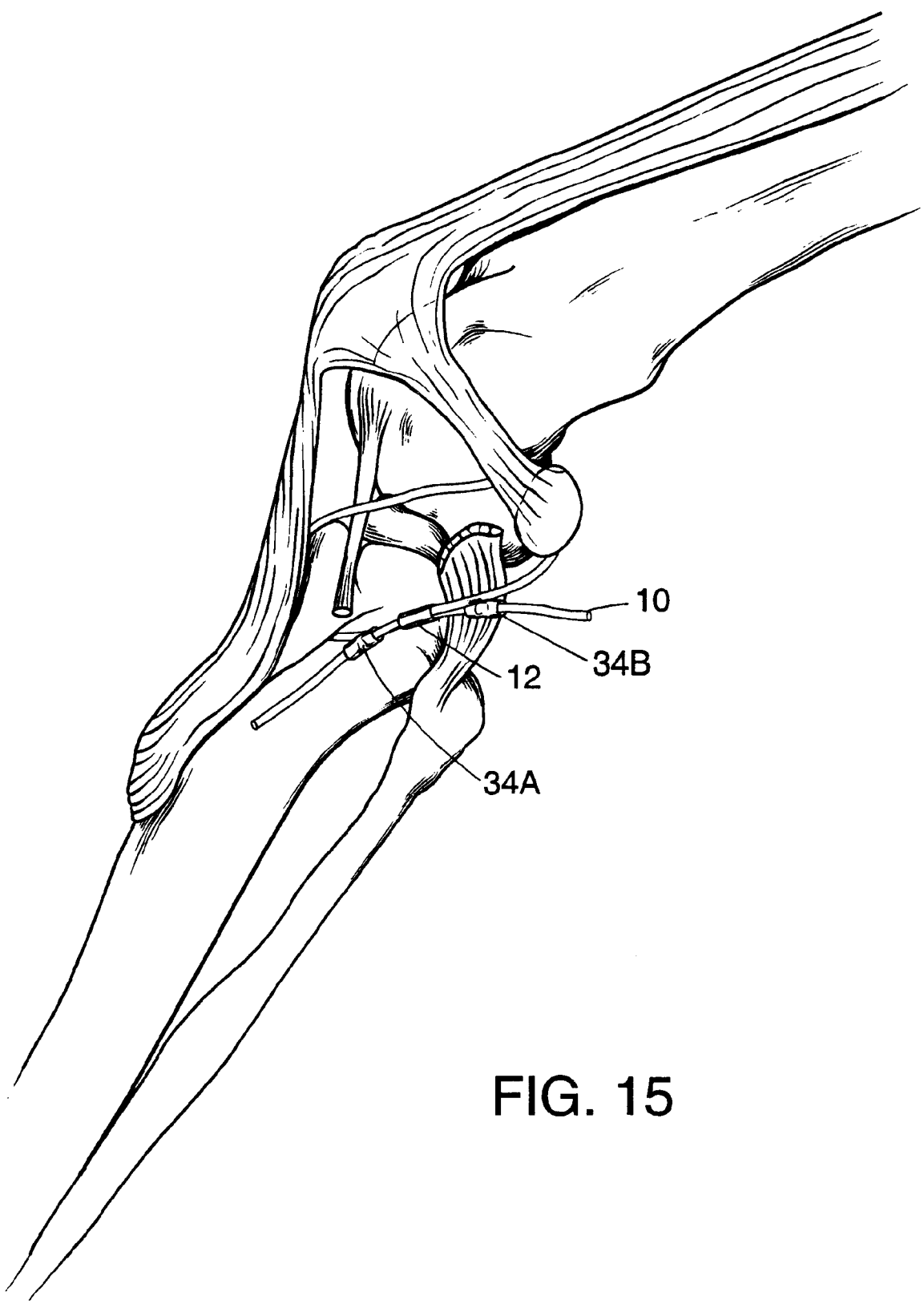
FIG. 15. illustration of step three of the surgical process.

FIG. 15 illustrates Step 3 of the procedure where the user slides each individual end of the suture 10 through an additional crimp tube, secondary crimp tubes 34A,34B, placing the additional crimp tubes 34A, 34B approximately 2–3 mm from the center or primary crimp tube 12. Once the additional crimp tubes 34A,34B are at the correct distance from the center crimp tube 12, the user can use the crimping tool 32 to firmly crimp these crimp tubes 34A, 34B. The user must make sure that the secondary crimp tubes 34A, 34B are firmly crimped. If they are not crimped enough they may slip during step 4. If they do slip, the surgeon can slide them back to their original location and crimp them a second time in a different location.

Figure 16:
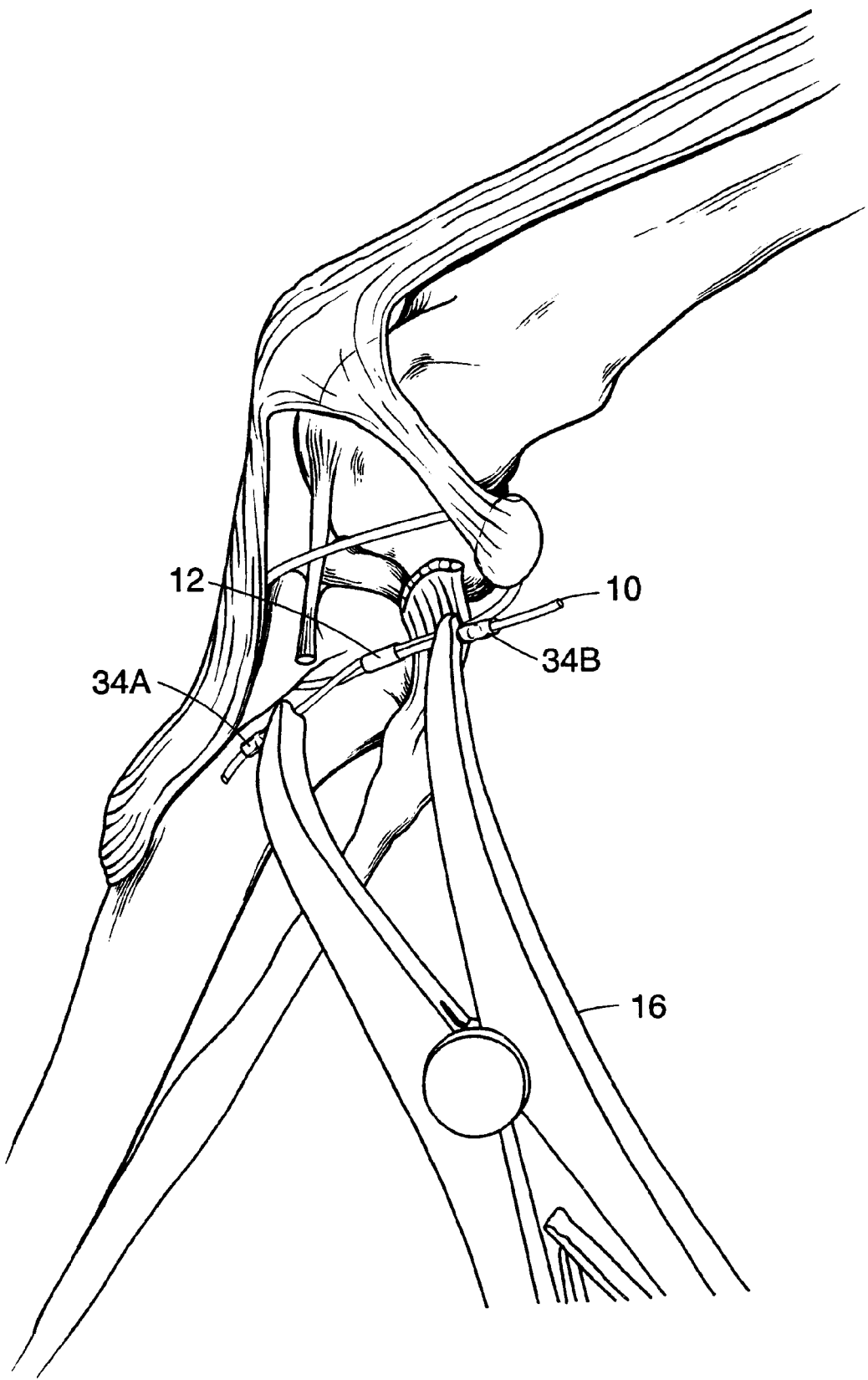
FIG. 16. illustration of step four of the surgical process.

FIG. 16 shows Step 4 of the procedure where a user slides the slotted tips of the tensioning device 16 over the suture 10, where the suture goes into the slots, on either side of the primary crimp tube 12. Each tip of the tensioning device 16 should be between the primary crimp tube 12 and one of the secondary crimp tubes 34A, 34B.

Squeezing the arms of the tensioning device 16 allows the ratcheting portion 30 of the device 16 to advance one click at a time. After each click the user should palpate the joint to feel for the appropriate loop tension. If too much tension is applied the fabella can be torn from the femur.

Figure 17:
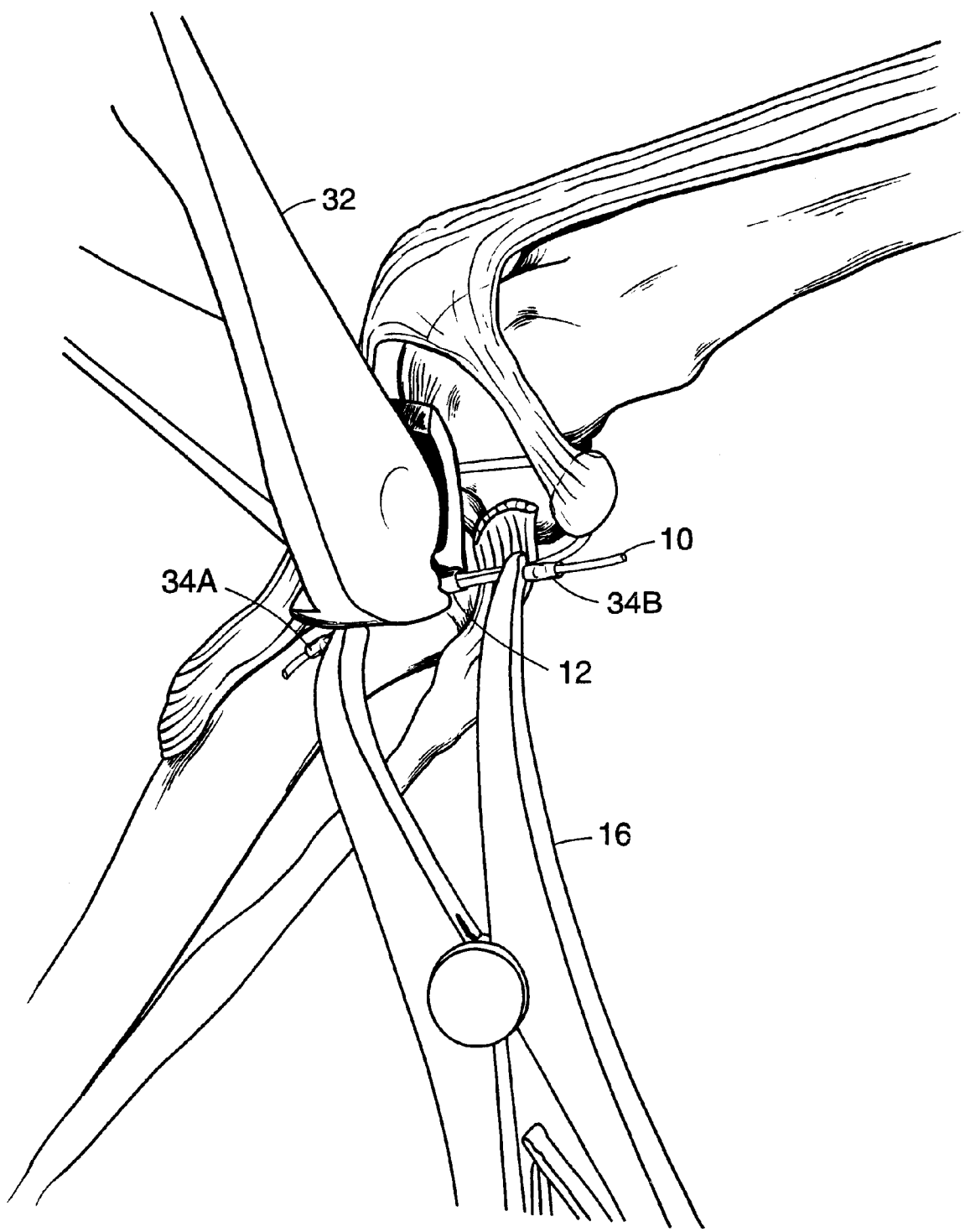
FIG. 17. illustration of step five of the surgical process.

FIG. 17 shows Step 5 of the procedure wherein once the desired loop tension is obtained, the user can crimp the primary crimp tube 12 using the crimping tool 32. For best results the user can crimp the primary crimp tube 12 once on both ends and once in the middle.

When crimping the crimp tubes 12, the user can ensure that the crimping tool 32 is fully closed such that the jaws of the crimping tool 32 touch when the tool is fully closed. This tool 32 is designed so that a user cannot over crimp the crimp tubes 12, and therefore, does not have to worry about applying too much pressure to the crimping tool 32.

Figure 18:
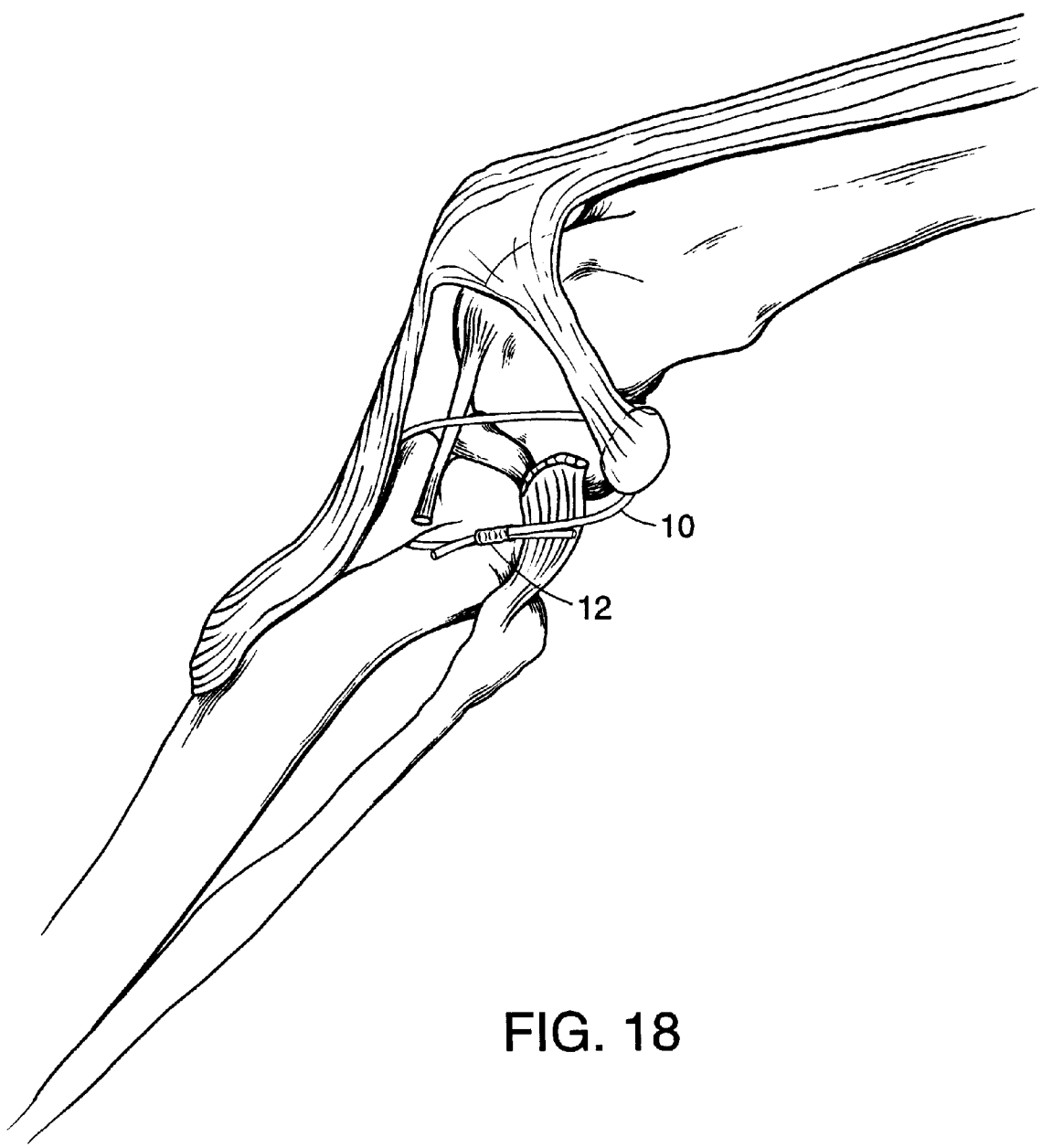
FIG. 18. illustration of step six of the surgical process.

FIG. 18 shows Step 6 of the procedure where the user removes the tensioning device 16 and cuts off the two secondary crimp tubes 34A, 34B. The user can leave approximately 3–5 mm of suture beyond each side of the primary crimp tube 12.

While this invention has been particularly shown and described with references to preferred embodiments thereof, it will be understood by those skilled in the art that various changes in form and details may be made therein without departing from the scope of the invention encompassed by the appended claims.

What is claimed is:

1. A crimping system comprising:
   at least one crimp tube for use in a surgical procedure, the at least one crimp tube having an aperture formed along a long axis of the crimp tube;
   a suture having a first suture end and a second suture end located within the aperture of the crimp tube, the first suture end and the second suture end being actuated to place the suture in tension; and
   a crimping tool having:
      a first arm having a proximal end and a distal end, the proximal end comprising a handle and the distal end comprising a first jaw,
      a second arm having a proximal end and a distal end, the proximal end comprising a handle and the distal end comprising a second jaw, the second arm hingedly connected to the first arm,
      first crimping member integral with the first jaw of the first arm, and
      a second crimping member integral with the second jaw of the second arm, the first crimping member and the second crimping member forming an oval-shaped cross section having a crimping area, the crimping area limiting the amount of deformation on the crimp tube when the crimping tool is placed in a closed position during a crimping procedure, the deformation securing the suture within the crimp tube and preventing a stress riser in the suture.

2. The crimping system of claim 1 wherein the crimping tool comprises a gap between the first jaw and the second jaw when placed in a closed position.

3. The crimping system of claim 1 wherein the first crimping member and the second crimping member comprise mirror image radii.

4. The crimping system of claim 1 wherein the crimping tool comprises a double action mechanism.

5. The crimping system of claim 1 wherein the first crimping member comprises a first width of 0.059 inches.

6. The crimping system of claim 1 wherein the second crimping member comprises a second width of 0.059 inches.

7. The crimping system of claim 1 wherein the crimp tube comprises an oval-shaped cross section corresponding to the oval-shaped cross section formed in the first crimping member and the second crimping member.

8. A method for crimping a crimp tube comprising:

attaching a suture to a biological component;

placing a first free end of the suture and a second free end of the suture within a crimp tube;

attaching a first crimp tube to the first free end of the suture and a second crimp tube to the second free end of the suture;

providing a tensioning device for engaging the first crimp tube and the second crimp tube and adjusting the tension of the suture;

providing a crimping tool having a first crimping member and a second crimping member, the first crimping member and the second crimping member forming an oval-shaped cross section having a crimping area; and crimping the crimp tube, the crimping area of the crimping tool limiting the amount of deformation to the crimp tube.

9. The method of claim 7 further comprising securing the first free end and the second free end of the suture within the crimp tube.

10. The method of claim 8 further comprising compressing the crimp tube in at least three locations.

11. The method of claim 8 further comprising compressing the crimp tube in not more than five locations.

12. The method of claim 8 further comprising preventing a significant stress riser at a crimp site on the suture.

13. A surgical instrumentation kit comprising:

a plurality of surgical crimp tubes including a first crimp tube for attachment to a first end of a suture, a second crimp tube for attachment to a second end of the suture and a third crimp tube for attachment to the suture between the first crimp tube and the second crimp tube;

a tensioning device for engaging the first crimp tube and the second crimp tube, engagement of the tensioning device adjusting the tension of the suture; and a crimping tool to crimp the third crimp tube onto the suture, the crimping tool having:
  a first arm with a proximal end and a distal end, the proximal end comprising a handle and the distal end comprising a first jaw,
  a second arm with a proximal end and a distal end, the proximal end comprising a handle and the distal end comprising a second jaw, the second arm hingedly connected to the first arm,
  a first crimping member integral with the first jaw of the first arm and
  a second crimping member integral with the second jaw of the second arm, the first crimping member and the second crimping member forming an oval-shaped cross section having a crimping area, the crimping area limiting the amount of deformation on a crimp tube when the crimping tool is placed in a closed position during a crimping procedure.

14. The surgical instrumentation kit of claim 13 wherein the surgical crimp tube comprises a long axis having a length so as to allow placement crimps along the length to achieve holding of the suture.

15. The surgical instrumentation kit of claim 13 wherein the surgical crimp tube comprises chamfered internal diameter edges such that the crimp tube will not damage the suture.

16. The surgical instrumentation kit of claim 13 wherein the surgical crimp tube comprises a biocompatible material.

17. The crimping tool of claim 13 wherein the crimping tool comprises a double action mechanism.

18. The surgical instrumentation kit of claim 13 wherein the first crimping member comprises a first width of 0.059 inches.

19. The surgical instrumentation kit of claim 13 wherein the second crimping member comprises a second width of 0.059 inches.

20. The surgical instrumentation kit of claim 13 wherein the crimp tube comprises an oval-shaped cross section corresponding to the oval-shaped cross section formed in the first crimping member and the second crimping member.

* * * * *